United States Patent [19]

Irmscher et al.

[11] Patent Number: 4,514,405
[45] Date of Patent: Apr. 30, 1985

[54] USE OF ADENOSINE DERIVATIVES AS ANTICONVULSANTS

[75] Inventors: Klaus Irmscher, Darmstadt; Jürgen Uhl, Seeheim, both of Fed. Rep. of Germany

[73] Assignee: Merck Patent Gesellschaft mit beschrankter Haftung, Darmstadt, Fed. Rep. of Germany

[21] Appl. No.: 573,178

[22] Filed: Jan. 23, 1984

Related U.S. Application Data

[63] Continuation-in-part of Ser. No. 303,295, Sep. 17, 1981, abandoned.

[51] Int. Cl.³ .................... A61K 31/52; A61K 31/70
[52] U.S. Cl. .................................................. 514/46
[58] Field of Search .................................. 424/180, 253

[56] References Cited

U.S. PATENT DOCUMENTS 2,881,164  5/1959  Kissman et al. ................. 536/26
3,506,643  4/1970  Thiel et al. ...................... 536/26

OTHER PUBLICATIONS

Skolnick, Federation Proceedings, vol. 39, Oct. 1980, pp. 3050–3055.
P. Skolnick et al., European Jour. Pharm., 67, (1980), pp. 179–186.
P. Skolnick et al., Life Science, vol. 23, pp. 1473–1480.
P. Skolnick et al., Pharmacology Biochemistry & Behavior, vol. 12, pp. 685–689.

Primary Examiner—Stanley J. Friedman
Attorney, Agent, or Firm—Millen & White

[57] ABSTRACT

Adenosine derivatives of formula I

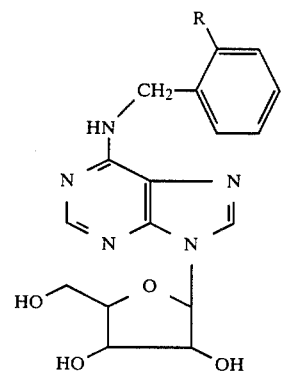

wherein R is H, F, Cl, Br or $CF_3$, and their physiologically acceptable acid addition salts, are valuable anticonvulsants.

14 Claims, No Drawings

USE OF ADENOSINE DERIVATIVES AS ANTICONVULSANTS

CROSS-REFERENCE TO RELATED APPLICATIONS

This application is a continuation-in-part application of U.S. Ser. No. 303,295 filed Sept. 17, 1981, now abandoned.

BACKGROUND OF THE INVENTION

The present invention relates to the use of adenosine derivatives as anticonvulsants.

Various anticonvulsant agents are known. For instance active compounds from the benzodiazepine group, for example diazepam, are used for such purposes. Although these substances are widely used, their administration has certain disadvantages. For example, an increase in appetite, a decrease in libido, menstruation disorders, dizziness and, at high doses, articulation disorders have been observed. Alcohol tolerance is also reduced.

SUMMARY OF THE INVENTION

Accordingly, it is an object of the present invention to provide other compounds which have more favorable properties and which can be used as anticonvulsants.

It is another object of this invention, in particular, to provide such compounds having a structure different from the benzodiazepines and which are well tolerated, do not have the side-effects mentioned, or have them only to a lesser degree.

Upon further study of the specification and appended claims, further objects and advantages of this invention will become apparent to those skilled in the art.

These objects have been achieved in one aspect of this invention by providing a psychopharmacological agent containing a compound of formula I

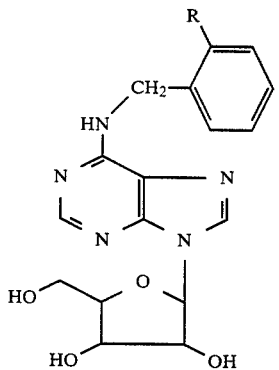

wherein R is H, F, Cl, Br, or $CF_3$, or one of the physiologically acceptable acid addition salts thereof.

In another aspect, this invention relates to the use of such compounds in combating stress conditions in the human or animal body.

The present invention in still another aspect relates to the use of adenosine derivatives of formula I or physiologically acceptable salts thereof for the preparation of anticonvulsant agents, in particular by a nonchemical route. Each of these compounds can be converted into a suitable dosage form together with at least one solid, liquid and/or semi-liquid excipient or auxiliary, and, if desired, in combination with one or more other active compound(s) compatible with the anticonvulsant agent.

The present invention in yet another aspect relates to an anticonvulsant agent, containing an adenosine derivative of formula I and/or one of its physiologically acceptable salts.

DETAILED DISCUSSION

The compounds of formula I and their pharmacologically acceptable salts are known (compare, for example, U.S. Pat. No. 2,881,164, furthermore German Auslegeschrift No. 1,670,171 corresponding to U.S. Pat. No. 3,506,643, all of whose disclosures are incorporated by reference herein). Some of their pharmacological actions are also already known, e.g., they cause an increase in coronary flow and an increase in the partial pressure of oxygen in the blood of the coronary veins.

However, it could not be seen from the statements in the literature that the compounds also, and above all, have anticonvulsant actions. This finding is unexpected and surprising.

Among the compounds of formula I, $N^6$-o-chlorobenzyladenosine (I, R=Cl) is preferred. The compounds of formula I can be prepared, for example, by reacting 6-chloro-, 6-bromo- or 6-methylthio-9-($\beta$-D-ribofuranosyl)-purine with benzylamine or with an o-R-benzylamine or by splitting off protective groups from compounds which otherwise correspond to formula I but in which the OH groups are present in the protected form, for example in the etherified or esterified form. Further details are given in the cited Auslegeschrift and patents.

The compounds for formula I can be converted into their physiologically acceptable acid addition salts, for example, into their hydrochlorides, hydrobromides, sulfates, nitrates or methanesulfonates, by treatment with the corresponding inorganic or organic acids, preferably strong inorganic or organic acids.

It has been found that the substances of this invention have valuable pharmacological properties, in particular anticonvulsant actions, coupled with a good tolerance. Furthermore, they have additional depressant actions on the central nervous system, in particular sedative, anxiolytic and muscle-relaxing properties.

These actions can be demonstrated, for example, by the usual tests such as cited by L. de Angelis (Meth. and Find. Exptl. Clin. Pharmacol., Volume 1, 1979, pages 129–155); the disclosure of this paper is incorporated by reference herein.

In detail, the anticonvulsive action can be demonstrated, for example, against convulsive and lethal doses of caffeine, bicuculline, picrotoxin, strychnine or pentetrazole to mice and rats, f.e. according to the method of Orloff et al., (Proc. Soc. Exptl. Biol. Med., Volume 70, 1948, pages 254 ff.

The anxiolytic action can be demonstrated, for example, using an unconditioned conflict test, such as has been described by A. S. Lippa et al. (Pharmacology, Biochemistry, Behavior, Volume 9 (1978) pages 853–856).

The muscle relaxing action can be demonstrated, for example, on mice in accordance with the method of Irwin (Psychopharmacologia, Volume 13, 1968, pages 222–257) or on rats in the muscle relaxation pair test (for the method, compare H. Müller-Calgan et al., described in H. P. Zippel (Editor), Memory and Transfer of Information, Plenum Press (New York-London), 1973, pages 97–100) using a study plan compiled by A. Ribbentrop and W. Schaumann (Arzneimittelforschung, Volume 15, 1965, pages 863–868). Hypnotic-potentiating properties, which can be demonstrated, for example, in mice and rats in accordance with the method of Janssen et al. (Journal of Medicinal and Pharmaceutical Chemistry, Volume 1, 1959, pages 281–297) and hypnotic-prolonging actions also occur. The substances furthermore have a tranquilizing action, which can be observed, for example in the spontaneous activity and the threatening behavior of rhesus monkeys [for the method, compare H. Müller-Calgan, Activ. nerv. sup. (Praha), Volume 16, 1974, pages 62–64].

A sedating action can also be detected on observation of the spontaneous motor activity of mice, the action being detected, for example, with the aid of the following method: groups of 6 mice each are placed in transparent plastic cages and are left in these cages for about 20 minutes in order to adapt to the new environment. The subtances are then administered intraperitoneally. The locomotive activity of the animals can be measured with a commercially available apparatus for measuring motility.

It has furthermore been found that the compounds of this invention show great affinity for the benzodiazepine receptors in the brain of mice.

The anticonvulsant agents of this invention can be used as medicaments in human medicine or veterinary medicine. Suitable excipients include organic or inorganic substances which are suitable for enteral (for example oral) or parenteral administration or topical application and which do not react with the compounds of formula I, for example water, vegetable oils, benzyl alcohols, polyethylene glycols, glycerol triacetate, gelatin, carbohydrates, such as lactose or starch, magnesium stearate and talc. Tablets, dragees, capsules, syrups, elixirs or drops are used, in particular, for oral application, suppositories are used for rectal administration and solutions, preferably oily or aqueous solutions, and furthermore suspensions, emulsions or implants are used for parenteral administration. The compounds can also be lyophilized, and the resulting lyophilizates can be used, for example, for the preparation of injection formulations. The formulations mentioned can be sterilized and/or can contain auxiliaries, such as lubricants, preservatives, stabilizers and/or wetting agents, emulsifiers, salts for influencing the osmotic pressure, buffer substances, colorants, flavoring substances and/or aroma generating substances. If desired, they can also contain one or more other active compounds, for example one or more vitamins and/or one or more other psychopharmacologically active substances, in particular benzodiazepines.

The present invention also relates to the use of an adenosine derivative of this invention in combating spasms, in particular of central origin, epilepsy, preferably epilepsies of the absence type, eclampsy, stress conditions, in particular psychic stress conditions (of an endogenic or exogenic origin) in the human or animal body, in particular excitation, tension, anxiety, psychoneurotic disorders, autonomic dystonia, psychosomatic disorders (in particular of the heart, circulation, stomach or intestines), sleep disorders and muscular tension (also in cases of rheumatism) and also to facilitate birth and during surgical intervention, and to their use in therapeutic treatment of the human or animal body.

The adenosine derivatives of this invention are as a rule administered analogously to known commercially available anticonvulsant and antiepileptic agents, for example diazepam, valproate or ethosuximide, and preferably in dosages of about 10 to 1,000 mg, in particular of 60 to 300 mg and above all of 150 to 200 mg per dosage unit. The daily dosage is preferably about 0.2 to 20 mg/kg of body weight. However, the specific dose for each particular patient depends on the usual highly diverse factors, for example on the activity of the particular compound employed, on the age, body weight, general state of health, sex and diet of the patient, on the point in time and method of administration, on the rate of elimination, on the medicament combination and on the severity of the particular illness to which therapy applies. Parenteral administration is preferred.

A determination of a satisfactory dosage of a compound of this invention to achieve a particular anticonvulsant action to treat a particular indication can be accomplished by conventional procedures, e.g., including a comparison of the relative activity of the compound of this invention with that of an analogous known anticonvulsant such as diazepam using a conventional pharmacological protocol for the given indication such as those mentioned above.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

Preparation examples:

EXAMPLE 1

A mixture of 28.6 g of 6-chloro-9($\beta$-D-ribofuranosyl)-purine, 14.2 g of o-chlorobenzyl amine, 400 ml of dimethylformamide, 400 ml of isopropanol and 50 ml of triethylamine is left to stand at 20° for 4 days. The mixture is evaporated, the residue is dissolved in chloroform, the chloroform solution is washed with 1% aqueous acetic acid and evaporated again and the residue is triturated with ether to give $N^6$-o-chlorobenzyl-adenosine (Ia). M.p.: 182°–183°.

EXAMPLE 2

Analogously to Example 1, equimolar amounts of 6-bromo-9-($\beta$-D-ribofuranosyl)-purine and benzyl amine give $N^6$-benzyl-adenosine (Ib). M.p.: 177°–179°.

EXAMPLE 3

Analogously to Example 1, using o-fluorobenzyl,o-bromobenzyl or o-trifluorobenzyl amine, respectively, the following are obtained:

$N^6$-o-fluorobenzyl-adenosine
$N^6$-o-bromobenzyl-adenosine
$N^6$-o-trifluoromethylbenzyl-adenosine, m.p. 160°–161°.

The examples which follow relate to pharmaceutical formulations which contain compounds of the formula I or their physiologically acceptable salts:

EXAMPLE A: Tablets

A mixture of 1.5 kg of Ia, 6 kg of lactose, 1.8 kg of potato starch, 0.3 kg of talc and 0.15 kg of magnesium stearate is pressed into tablets in the customary manner, such that each tablet contains 150 mg of active compound.

EXAMPLE B: Dragees

Tablets are pressed in a manner analogous to that in Example A, and are then covered in the customary manner with a coating of sucrose, potato starch, talc, tragacanth and colorant.

EXAMPLE C: Capsules

Hard gelatin capsules are filled with 3 kg of Ib in the customary manner, such that each capsule contains 300 mg of active compound.

EXAMPLE D: Ampoules

A solution of 1 kg of Ia in 30 l of doubly distilled water is filtered under sterile conditions and ampoules are filled with the solution, the solution is lyophilized under sterile conditions and the ampoules are sealed under sterile conditions. Each ampoule contains 50 mg of active compound.

EXAMPLE E

The procedures of Examples A-D are repeated using pharmacologically acceptable salts of Ia or Ib in place of the compound of formula I.

EXAMPLE AA

The compounds of this invention can be administered to patients, e.g., humans, suffering from any of the foregoing indications or other related indications such as those for which diazepam (Valium) is conventionally administered. Appropriate dosages can be conventionally determined as indicated above. Determination of treatment duration and general regimen is by conventional considerations such as those used in conjunction with diazepam therapy taking into account the differences in potency and other actions involved in each case.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of achieving an anticonvulsant effect in a patient suffering from an indication which can be treated by achieving such an effect, which comprises administering to such a patient an amount of a compound of the formula

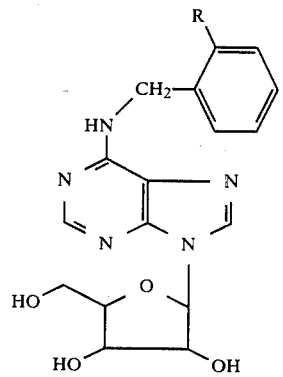

wherein R is H, F, Cl, Br or $CF_3$ or a physiologically acceptable acid addition salt thereof, effective to achieve an anticonvulsant effect in the patient which relieves the indication.

2. A method of claim 1 wherein the amount of the compound administered is 0.2 to 20 mg/kg/day in unit doses of 10-1.000 mg.

3. A method of claim 2 wherein the administration is parenteral.

4. A method of claim 1 wherein the indication is epilepsy.

5. A method of claim 1 wherein the patient is not suffering from an indication which is treatable by increasing the coronary flow or increasing the partial pressure of oxygen in the blood.

6. A method of claim 1 wherein R in the compound administered is Cl.

7. A method of claim 1 wherein R in the compound administered is H.

8. A method of claim 1 wherein the indication is eclampsy or spasms derived from a stress condition.

9. A method of claim 8 wherein the indication is spasms derived from a psychic stress condition which is excitation, tension, anxiety, a psychosomatic disorder, a sleep disorder, or muscular tension.

10. A method of achieving a CNS-depressant effect in a patient in need of such treatment, which comprises administering to such a patient an amount of a compound of the formula

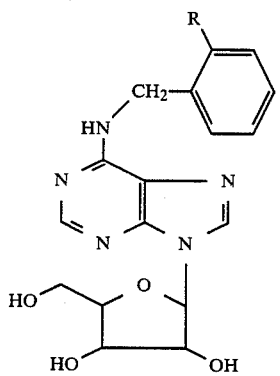

wherein R is H or Cl or a physiologically acceptable acid addition salt thereof, effective to achieve a CNS-depressant effect in the patient.

11. A method of claim 10 wherein the CNS-depressant effect is a sedative, anxiolytic or muscle-relaxing effect.

12. A method of claim 4 wherein R in the compound administered is Cl.

13. A method of achieving a pharmacological effect in a patient not suffering from an indication which is treatable by increasing the coronary flow or increasing the partial pressure of oxygen in the blood, and is suffering from an indication similarly treatable as CNS-depression or spasms, comprising administering to said patient a compound of the formula

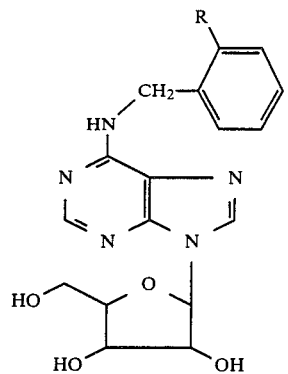

wherein R is H, F, Cl, Br or $CF_3$ or a physiologically acceptable acid addition salt thereof.

14. A method of claim 2 wherein R in the compound is administered is Cl.

* * * * *